United States Patent [19]

Snipes et al.

[11] Patent Number: 4,744,976
[45] Date of Patent: * May 17, 1988

[54] ERODIBLE MATRIX FOR SUSTAINED RELEASE BIOACTIVE COMPOSITION

[75] Inventors: Wallace C. Snipes, Pine Grove Mills; Stephen J. Wagner, Pennsylvania Furnace, both of Pa.

[73] Assignee: Zetachron, Inc., State College, Pa.

[ * ] Notice: The portion of the term of this patent subsequent to Dec. 16, 2003 has been disclaimed.

[21] Appl. No.: 918,294

[22] Filed: Oct. 14, 1986

Related U.S. Application Data

[63] Continuation-in-part of Ser. No. 633,604, Jul. 23, 1984, Pat. No. 4,629,621.

[51] Int. Cl.⁴ ............................................. A61J 3/10
[52] U.S. Cl. ................................... 424/408; 424/418; 424/493; 424/502; 428/402.24; 428/401; 428/379
[58] Field of Search ................ 424/19, 22; 428/402.24

[56] References Cited

U.S. PATENT DOCUMENTS

| | | | |
|---|---|---|---|
| 3,336,155 | 8/1967 | Rowe | 424/19 |
| 3,634,584 | 2/1969 | Poole | 424/19 |
| 3,641,236 | 2/1972 | Coppen et al. | 424/19 |
| 4,333,919 | 6/1982 | Kleber et al. | 424/15 |
| 4,346,709 | 8/1982 | Schmitt | 424/19 |
| 4,351,825 | 9/1982 | Sothmann et al. | 424/19 |

Primary Examiner—Morton Foelak
Assistant Examiner—M. L. Moore
Attorney, Agent, or Firm—Vorys, Sater, Seymour and Pease

[57] ABSTRACT

A sustained release composition for releasing a biologically active compound into an aqueous liquid environment comprises the biologically active compound dispersed in a bioerodible matrix, the matrix comprising a mixture of (a.) 5% to 99.5% by weight of a solid water-dispersible polyether diol having a molecular weight from about 1000 to about 20,000, and (b.) 95 to 0.5% by weight of an erosion rate modifier component comprising a combination of stearyl alcohol and stearic acid.

Dosage forms comprising the erodible matrix are prepared by molding, particularly by injection molding.

85 Claims, 4 Drawing Sheets

FIG. 1

ERODIBLE MATRIX FOR SUSTAINED RELEASE BIOACTIVE COMPOSITION

REFERENCE TO RELATED APPLICATION

This application is a continuation-in-part application of copending application Ser. No. 633,604, filed July 23, 1984, now U.S. Pat. No. 4,629,621.

BACKGROUND OF THE INVENTION

1. Field of the Invention

This invention relates to sustained release compositions for bioactive compounds and more particularly to sustained release oral dosage forms incorporating a drug in an erodible matrix.

2. Description of the Prior Art

In chemotherapy of diseases it is frequently desirable to maintain the concentration of the therapeutic drug at a relatively constant level in the blood or organ being treated. One method for achieving this goal is to administer the drug continously at a rate which balances its rate of metabolism and/or excretion. In a hospital environment this goal can be attained by intravenously administering a drug, but outside of such an environment this method of administration is impractical in the great majority of cases. Consequently, the most common method of administering a drug is orally, in the form of tablets, capsules, and the like, which preferably have sustained release characteristics. The drug released therefrom is usually absorbed from the gastrointestinal tract and reaches the target organ via the blood stream.

Among the various types of sustained release dosage forms which have been developed are erodible matrices, i.e., dosage forms wherein the drug is entrapped in a matrix which upon ingestion gradually decomposes in the intestinal fluid thereby releasing the drug for absorption. An example of such a dosage form is found in Schmitt, U.S. Pat. No. 4,346,709, wherein the device comprises a drug dispersed in a bioerodible polymer which is a poly(orthoeter) or a poly(orthocarbonate) containing an erosion rate modifier. The erosion rate modifiers of Schmitt are mono- and polybasic organic acids which adjust the pH at the surface of the erodible matrix to accelerate or retard the decomposition of the polymer in the gastric or intestinal environment.

In a further example, Sothmann, et al., in U.S. Pat. No. 4,351,825, discloses a sustained release oral dosage form wherein a drug is dispersed in a matrix of a water-insoluble polymethacrylate, e.g., a copolymer of acrylic and methacrylic acid esters containing quaternary ammonium groups or a copolymer of methacrylic acid and methyl methacrylate, which has an anionic character. The granules of the matrix material are mixed with the active drug and an erosion rate modifier which is an ester of a long chain fatty acid with glycerine or a long chain alcohol.

Additionally, Kleber, et al., in U.S. Pat. No. 4,333,919, disclose controlled release formulations comprised of a drug mixed with a copolymer of lactic and glycolic acids. The formulations may also contain adjuvants such as glyceryl distearate. The formulations are primarily intended for growth stimulant for ruminants. Accordingly, they are administered by filling open-ended steel cylinders with the formulations and placing the cylinders in the rumen of the animal. The filled steel cylinders remain in the rumen, and the growth stimulant is gradually released as the matrix is eroded by the rumen fluids.

It seems evident from these disclosures, and others, that the erodible formulations of the prior art have generally required specially prepared polymers, and that the rate of erosion of such polymers cannot always be adjusted to provide for preferential release of the drug in a particular portion of the gastrointestinal tract, e.g., in the stomach or small intestine.

Therefore, a need has continued to exist for an erodible matrix, prepared from readily available materials which are suitable for sustained release pharmaceutical formulations, wherein the rate of erosion can be substantially controlled.

SUMMARY OF THE INVENTION

Accordingly, it is an object of this invention to provide an oral, sustained release dosage form.

A further object is to provide an oral, sustained release dosage form incorporating an erosion rate modifier substance.

A further object is to provide an oral, sustained release dosage form whose formulaton and/or structure can be adjusted to release its medication either in the stomach or the small intestine.

A further object is to provide a sustained release composition containing a bioactive compound which is released by erosion of the matrix in an aqueous liquid environment.

A further object is to provide a liquid-erodible composition wherein the rate of erosion can be adjusted by incorporation of an erosion rate modifier.

A further object is to provide a liquid-erodible composition wherein the rate of erosion can be adjusted to vary with the pH of the surrounding aqueous liquid.

Additional objects will become apparent from the description of the invention which follows.

The objects of the invention are achieved by a composition capable of being eroded in an aqueous liquid environment comprising (a.) about 5% to about 99.5% by weight of a solid water-dispersible polyether diol having a molecular weight from about 1000 to about 20,000, and (b.) about 95% to about 0.5% of an erosion rate modifier which is an amphiphilic compound insoluble in the aqueous liquid.

A sustained release dosage form according to the invention comprises a matrix of the erodible composition of the invention having dissolved or dispersed therein a bioactive compound to be released over a period of time.

DETAILED DESCRIPTION OF THE INVENTION AND PREFERRED EMBODIMENTS

The property of the composition of this invention which makes it useful in sustained release preparations of bioactive material is its erodible character. Because it is the surface of an erodible composition which dissolves or decomposes into the surrounding medium and the eroding liquid does not substantially penetrate its structure, it is possible to achieve superior control of the dissolution rate of the solid composition, so that it may be used in a variety of applications.

The erodible matrix of this invention is especially suitable for incorporating a drug to be administered over a period of time via the intestinal absorption route. It is formed from a composition comprising solid water-dispersible polyether diol and an amphiphilic erosion rate modifier, and the kinetics of its drug release are determined by the properties of the matrix and the shape of the dosage form. Accordingly, the rate of release can be controlled by varying the size and shape of the dosage form as well as the proportion and type of the erosion rate modifier.

One particular dosage regimen wherein the controlled release composition of this invention is useful is in the administration of drugs which have a relatively short biological half-life in the body. Such drugs can be incorporated into a dosage form made from the erodible controlled release matrix of this invention which is designed to release the drug continuously over a period of 6 to 18 hours in order to provide a continuously supply of the drug to the patient and thereby maintain a therapeutic level of the drug in the patient. Such relatively long-lived dosage forms will have an erodible matrix of the invention which incorporates a relatively large amount of the release rate modifier, e.g., 60% to 20% by weight of the composition. Another dosage regimen which can make use of the controlled release matrix of this invention is found in the case of drugs which have a sufficient half-life, e.g., up to 18 hours, so that sustained release of the medication is not necessary to maintain a therapeutic level in the patients plasma or the target organ. However, when long-lasting drugs of this type are given in a dosage form which releases the medication all at once, the initial concentration of the drug in the patients bloodstream may exceed the therapeutic range and result in undesirable side effects. With such drugs it is desirable to control the rate of absorption to avoid an initial overdose, and release of the drug over a period of 30 minutes to two hours will accomplish this goal. For this relatively rapid, but controlled, release the amount of release rate modifier will be present in amounts of about 10% to about 0.5% by weight.

The solid water-soluble polyethylene glycol component of the erodible matrix of this invention may include any polyethylene glycol (PEG) having a molecular weight from about 1000 to about 20000. All of the polyethylene glycols in this range are solid materials which are soluble in water and which will slowly dissolve when in contact with an aqueous medium. Mixtures of polyethylene glycols of different molecular weights may also be used. A preferred PEG is that havng a molecular weight of about 8000.

The polyethylene glycol component of the erodible matrix may be present in amounts ranging from about 5% to about 99.5% by weight of the erodible matrix. When a relatively slow release composition is desired, the proportion of the polyether diol component will range from about 40% to about 80% by weight, while when a relatively rapid controlled release is desired, the proportion of the polyether diol component will be from about 90% to about 99.5% by weight.

The erosion rate modifier is an insoluble amphiphile, that is, a material whose molecule possesses a hydrophilic portion and a lipophilic portion, usually located at opposite ends of a relatively elongated molecule. The presence of lipophilic portions in the erosion rate modifier slows down the rate at which the matrix is eroded when in contact with an aqueous liquid environment. Therefore, the rate of erosion can be slightly retarded by incorporating relatively small amounts of erosion rate modifier and greatly retarded by incorporating relatively large amounts of erosion rate modifier.

The erosion rate modifier can also be chosen to vary the rate of erosion under varying conditions of pH. For example, if the erosion rate modifier is a long chain fatty acid such as myristic acid, the erosion rate of the matrix will be relatively slow in acid media wherein the carboxyl group of the myristic acid is not ionized and the amphiphilic molecule is accordingly relatively hydrophobic. On the other hand, under basic conditions the carboxyl group is ionized, and therefore hydrophilic, which makes the erosion rate considerably faster. Evidently, a dosage form made from such a formulation releases relatively little of a drug in the acidic environment of the stomach, but subsequently more freely releases the drug in the basic environment of the small intestine. In the event that erosion of the matrix in the stomach is desired, then erosion rate modifiers having basic groups which are ionized under acidic conditions can be incorporated in the matrix composition.

The erosion rate modifier can also be chosen to compensate for the effects of charged form of the bioactive compound on the erosion rate. When the bioactive compound, e.g., a drug, is present in the matrix of the invention in amounts greater than about 2-3% by weight of the total composition, the ionic character of the drug can affect the rate of erosion at various pH's of the eroding environment. For, example if the erodible matrix contains a basic drug, which will assume a positive charge in the acidic environment of the stomach, thereby increasing the erosion rate, an acidic erosion rate modifier, e.g., a long chain fatty acid such as myristic acid, may be used as an erosion rate modifier. The acid will remain un-ionized in the acidic environment of the stomach and thereby act to retard the erosion rate and counterbalance the effect of the basic drug.

Use of erosion rate modifiers devoid of ionizable hydrophilic groups, such as long chain aliphatic alcohols, results in an erodible matrix whose rate of erosion is not greatly affected by the pH of the environment.

The erosion rate modifier may be present in the erodible compositions of this invention in amounts of about 95% to about 0.5% by weight. When a relatively slow-release matrix is desired, the erosion rate modifier will preferably constitute about 60% to about 20% by weight of the composition, while when a relatively rapid controlled release matrix is desired, the erosion rate modifier will be present in a proportion of about 10% to about 0.5% by weight.

Suitable erosion rate modifiers include $C_{12}$–$C_{20}$ fatty acids, such as lauric acid, myristic acid, palmitic acid, stearic acid, and arachidic acid; $C_{12}$–$C_{20}$ alcohols, such as lauryl alcohol, myristyl alcohol, palmityl alcohol, stearyl alcohol and arachidyl alcohol, amphiphilic esters of fatty acids with glycerol, particularly monoesters of $C_{12}$–$C_{20}$ fatty acids such as glyceryl monopalmitate, $C_{12}$–$C_{20}$ amines such as lauryl amine, myristyl amine, palmityl amine, stearyl amine and arachidyl amine, and amides of $C_{12}$–$C_{20}$ fatty acids.

In various dosage forms embodiments of this invention, the rate of drug release can be controlled by varying the shape of the dosage form or by coating the surface of the dosage form. For example, an erodible dosage form of the invention may have a cylindrical shape wherein the height of the cylinder is much greater than the diameter, so that most of the area of the cylinder exposed to the erosive action of the aqueous liquid medium is constituted by the curved peripheral surface of the cylinder. When such a cylinder is immersed in a liquid medium the peripheral surface of the cylinder will be eroded. As the diameter of the cylinder decreases through its erosion, the area of the periperal surface exposed to the erosive action of the aqueous liquid environment decreases proportionally. Therefore, the dosage form will erode at a rate which will provide approximately first order drug release kinetics. If a cylindrical dosage form has a relatively small height compared with its diameter, so that most of the exposed area is provided by the bases of the cylinder, the eroding surface area of the dosage form will not change greatly as erosion proceeds. In this case of the rate of drug release will be substantially constant, i.e., the drug release kinetics will be approximately zero order.

In another embodiment, the surface of the dosage form can be partially coated with a liquid-impervious coating so that only certain surfaces of the dosage form are exposed to the erosive action of the medium. This method also allows for adjusting the kinetics of drug release. For example, if a cylindrical dosage form is coated on its curved peripheral surface so that only the ends of the cylinder are exposed to the erosive action of the medium, the area of the dosage form exposed to erosive action will not change with time. In this embodiment, therefore, the drug will be released at a constant rate, i.e., the release kinetics will be approximately zero order.

In order to assure that the rate of drug release will actually remain substantially constant for this coated cylindrical dosage form, it is necessary that the coating be non-self-supporting. If the coating is self-supporting it will extend beyond the ends of the cylindrical portion remaining after a portion of the dosage form has been eroded. This extension will interfere with the access of the eroding aqueous liquid medium to the ends of the cylinder and will, accordingly, affect the kinetics. Therefore, the preferred coating for this type of dosage form is a very thin friable material which is not self-supporting. With such a coating, any portion extending beyond the end of the cylinder after the immediately underlying matrix has been eroded will be broken off as the dosage form is subjected to agitation in the gastrointestinal tract, thus keeping the uncoated ends of the cylinder fully exposed to the erosive action of the medium.

In most cases it will be convenient to apply the coating material in the form of a melt which solidifies by cooling on the surface of the dosage form. Preferred coating materials are long chain fatty acids having 12 to 20 carbon atoms. Such acids include lauric acid, myristic acid, palmitic acid, stearic acid and arachidic acid. The thickness of the coating will typically be from about 0.02 mm to about 0.5 mm.

Additional ingredients can be incorporated into the erodible composition of this invention to modify and/or control the properties of the composition. For example, in order to improve the compatibility between the polyethylene glycol and the erosion rate modifier and prevent phase separation when the molten composition is cooled, a modified polyethylene glycol wherein the OH groups at one or both ends are esterified with long chain fatty acids may be added to the mixture. Suitable long chain fatty acids are aliphatic fatty acids having from about 12 to about 20 carbon atoms such as those disclosed above. Preferred polyethylene glycols to be used in preparing the esterified PEG compatibility enhancers are those having a molecular weight from about 200 to 10000, preferably from about 200 to about 2000. PEG 400 and PEG 600 are particularly preferred materials for preparing the esterified PEG's. For example, the esterified PEG's may be the monoesters and preferably the lauric or stearic ester. More preferred esters are the diesters, particularly the dilauroyl and distearoyl esters. These modified polyethylene glycols are prepared by conventional esterification procedures well known to those skilled in the art, such as reacting the polyethylene glycol with the acid chloride of the chosen acid. The modified polyethylene glycol may be incorporated into the compositions of this invention in any effective amounts, such as in an amount up to about 10% by weight, preferably from about 0.1% to about 10% by weight, and particularly about 2% by weight.

Starch may also be added to the erodible mixture of this invention as a disintegrant in order to adjust the erosion rate. The starch tends to enhance the erodible characteristics of the composition by causing the solid material to dissolve from the surface without penetration of the aqueous liquid into the interior of the solid form. Any type of starch may be used, particularly a pharmaceutically acceptable and readily available form of starch, such as cornstarch. Starch may be present in amounts of from about 5% by weight to about 60% by weight, preferably from about 10% by weight to about 50% by weight, and more preferably from about 20% by weight to about 40% by weight.

Molding adjuvants may also be added to the compositions of this invention. It has been found that the addition of a polyethylene oxide (PEO) having a molecular weight (MW) from about 100,000 to about $5 \times 10^6$ has beneficial effects on the viscosity and plasticity of the composition. This provides for easier mold filling and release of molded forms from the solid, especially when molded dosage forms of this invention are prepared by injection molding. The PEO may be present in an effective amount up to about 2% by weight, preferably from about 0.5% by weight to about 1% by weight, and most preferably about 0.1% by weight. It will be appreciated by those skilled in the art that injection molding of compositions containing a relatively large number of ingredients, such as the compositions of this invention, is not common. Hence, some experimentation may be required to determine the exact amount of molding adjuvant needed for a given composition.

For water-soluble drugs and bioactive compounds, a preferred matrix which provides uniform release kinetics under conditions of varying pH and for a great many different drugs comprises a composition according to the invention wherein the release rate modifying agent is a combination of stearyl alcohol and stearic acid. The amounts of stearyl alcohol may range from about 4% to about 13% by weight and the amount of stearic acid may range from about 4% to about 15% by weight. It is also preferred in this composition to include up to about 45% by weight of a hydratable material which serves to increase the rate at which water penetrates into the composition to dissolve the water soluble or water-dispersible components, i.e., the PEG's, polyethylene oxide-polypropylene oxide block copolymers, drugs, and the like. Such hydratable materials include starch, e.g., corn starch, and colloidal silica. It is also preferred that this composition incorporate a long chain aliphatic monoester of a PEG having a molecular weight of about 400, e.g., PEG 400 monostearate, in amounts of about 2% to about 8% by weight in order to improve the compatibility of the PEG with the amphiphilic erosion rate modifier as discussed above.

In addition to the use of PEG (400) monostearate or another long chain aliphatic monoester of PEG to improve the compatibility of the PEG with the amphiphile erosion rate modifier in the matrix, PEG (400) monostearate is also useful as an erosion rate modifier when used in conjunction with amphiphilic erosion rate modifiers, e.g., a fatty acid or fatty alcohol, or the preferred combination of stearic acid the stearyl alcohol. The amount of PEG (400) monostearate required to function as an erosion rate modifier may range from 2 to 8% by weight.

The erodible matrix of this invention is useful wherever controlled release of a material into an aqueous liquid environment is desired. Such an erodible material may be used, for example, without an incorporated drug as a coating for a substance designed for a delayed dissolution after immersion in an aqueous liquid. It may serve a similar function when employed as a plug for a container intended to release a material on a delayed-action basis when immersed or contacted with an aqueous liquid.

The erodible composition of this invention may also contain an ecological agent dispersed therein in order to provide for gradual release of the ecological agent into an aqueous liquid environment. An ecological agent is defined for purposes of this invention as a non-pharmaceutical substance which has a biological effect on plants or animals in the environment. An ecological agent may be a pesticide, such as an insecticide or herbicide, a fertilizer, a pheromone, a plant growth hormone, or the like. When dosage forms made from compositions containing such bioactive ingredients contact an aqueous liquid environment the bioactive materials are gradually released into the environment. Accordingly, the compositions of this invention are useful for releasing such ecological agents into bodies of water or into a land environment where they may release their active agents by contact with rain or standing water, so as to maintain an effective concentration of the agent in the environment for a relatively long period of time.

It is preferred to use the erodible matrix of this invention as a carrier for sustained release pharmaceuticals administered orally to individuals in need of a relatively constant concentration of medication. The drugs may be locally or systemically acting drugs, and may be selected from among any group wherein a steady concentration of the drug in the organism is desired. Accordingly, the drug may be selected from among analgesic, anorexic, antiarthritic, antibacterial, antibiotic, anticonvulsant, anti-depressant, antidiabetic, anti-fungal, antihistaminic, anti-hypertensive, anti-inflammatory, anti-neoplastic, antiparkinsonism, anti-pyretic, anticholinergic, anti-inflammatory, anesthetic, antimicrobial, antiviral, anti-ulcer, bronchodilator, cardiovascular, contraceptive, central nervous system affecting, inotropic, vasodilator, vasoconstrictor, decongestant, diuretic, hypoglycemic, hormone, hypnotic, hematinic, electrolyte supplement, germicidal, muscle relaxant, parasympathetolytic, parasympathetomimetic, tranquilizer, ophthalmic, psychostimulant, vitamin, and the like drugs. The drugs can be administered in the form of the parent compound as well as in the form of pharmaceutically acceptable salts, and precursors.

Preferred drugs for use in the dosage forms prepared according to the invention include clonidine, theophylline, dipyridamole, hydrochlorothiazide, scopolamine, indomethacin, furosemide, potassium chloride, pseudoephedrine and the like.

The drug to be released from the dosage form of the invention may be incorporated into the erodible matrix simply by dissolving it in the molten matrix or mixing it therewith.

The proportions of drug and erodible matrix in the dosage forms of this invention may vary within wide limits. Because some drugs are effective in very small doses and others require relatively large doses for effect, the proportions will vary depending on the amount of drug which must be incorporated into the unit dosage form. Accordingly, the drug may be constitute in an effective amount up to about 70% by weight of the composition. More preferably the drug will constitute from about 0.1% to about 50% by weight of the composition, with the balance being the erodible matrix.

The unit dosage forms of the invention can be prepared by conventional procedures such as compression molding, tableting, extrusion, and injection molding. It is preferred that the dosage forms of the invention be non-porous in order that the erosion will proceed from the surface of the dosage form. Such non-porous dosage forms are best prepared by solidification of a molten form of the composition containing all ingredients of the composition, and injection molding is especially useful for that purpose. Indeed, the dosage forms of the invention are especially adapted to production by injection molding because the erodible matrix composition of the invention has a relatively low melting temperature, and hence the injection molding can be carried out at a temperature which is not detrimental to the drug contained in the dosage form.

The preferred dosage forms of the invention have a cylindrical shape with a diameter of about 3 mm to about 8 mm, and preferably about 5 mm. The length of the cylindrical dosage form is typically about 5 mm to about 20 mm, and is preferably about 10 mm. The preferred dosage forms may be coated on their peripheral cylindrical surfaces with a liquid-impervious non-self-supporting coating as discussed above.

The sustained release compositions of this invention are prepared by the following general procedure.

A premeasured amount of a polyethylene glycol is melted in a vessel, e.g., a kettle provided with a steam jacket or a heating mantle and equipped with a stirring mechanism. A temperature of about 85° C. is sufficient to melt any of the polyethylene glycols. The premeasured amount of the insoluble amphiphile is then added either as a molten liquid or as a solid. It is preferred to melt the insoluble amphiphile and add it slowly to the stirred molten PEG. The long chain fatty amphiphiles useful in the compositions of this invention are generally molten at the temperature of the molten PEG and can be readily mixed with the PEG. Other ingredients, such as disintegrants (e.g., starch), molding adjuvants (e.g., polyethylene oxide), and the like are then added and the mixture is thoroughly blended. The bioactive agent, drug or the like is then added and mixed into the molten mixture. Dosage forms may then be formed directly from the molten mixture by the procedures outlined above.

The invention will now be further elucidated by the following examples which are included by way of illustration only and are not intended to be limiting. In the examples all percentages and parts are weight unless otherwise specified.

EXAMPLE 1

This example illustrates the preparation of dosage forms of the invention containing polyethylene glycols of various molecular weights.

A series of compositions were prepared having the following compositions:

| A | PEG-1000 | 37.5% |
|---|---|---|
|   | Myristic acid | 15% |
|   | Starch | 22.5% |
|   | Indomethacin | 25% |
| B | PEG-4000 | 37.5% |
|   | Myristic acid | 15% |
|   | Starch | 22.5% |
|   | Indomethacin | 25% |
| C | PEG-8000 | 37.5% |
|   | Myristic acid | 15% |
|   | Starch | 22.5% |
|   | Indomethacin | 25% |
| D | PEG-20,000 | 37.5% |
|   | Myristic acid | 15% |
|   | Starch | 22.5% |
|   | Indomethacin | 25% |

Cylindrical dosage forms were molded from the compositions A–D by pouring the molten compositions into open-ended plastic molds made of polyethylene having a diameter of about 6 mm and allowing the melt to cool to room temperature. The solidified composition was then extruded from the molds and cut into lengths to prepare cylindrical dosage forms. In this way dosage forms having a diameter of about 6 mm and a length of about 14 mm and weighing about 0.44 g each were prepared.

The sustained release properties of the dosage forms were then tested by the following procedure:

Simulated intestinal fluid (SIF) was prepared by the following procedure:

(1) 6.8 g of monobasic potassium phosphate were dissolved in 250 ml of water.
(2) 190 ml of 0.2N NaOH was added with stirring.
(3) 400 ml of water and 10 ml of pancreatin were added.
(4) The pH of the solution was adjusted with 0.2N NaOH to 7.5+0.1.
(5) The solution was diluted with water to 1000 ml.

Each of the cylindrical dosage forms was placed in 80 ml of SIF at 37° C. and subjected to gentle agitation. The amount of drug released was monitored by measuring the optical density of the aqueous medium at an absorption peak of indomethacin at intervals using an ultraviolet spectrophotometer. Each of the dosage forms was found to release the drug gradually over a period of several hours.

Cylindrical dosage forms of the same size and shape as above were prepared from each of the compositions A–D, but these cylinders were coated on their cylindrical surfaces with myristic acid by dipping the cylinders in molten myristic acid, withdrawing the cylinders and allowing the myristic acid coating to cool and harden, and then scraping the coating from the ends of the cylinders. These dosage forms were tested in SIF by the same procedure as the uncoated dosage forms. They also were found to release the drug over a period of several hours with the drug release occurring at an approximately constant rate.

EXAMPLE 2

This example illustrates variation of the fatty acid erosion rate modifier.

Several dosage forms were prepared by the procedure of Example 1 having the following compositions:

| A | PEG-8000 | 37.5% |
|---|---|---|
|   | Myristic acid | 15% |
|   | Starch | 22.5% |
|   | Indomethacin | 25% |
| B | PEG-8000 | 37.5% |
|   | Palmitic acid | 15% |
|   | Starch | 22.5% |
|   | Indomethacin | 25% |
| C | PEG-8000 | 37.5% |
|   | Stearic acid | 15% |
|   | Starch | 22.5% |
|   | Indomethacin | 25% |

The dosage forms were tested by the procedure of Example 1 and were found to release the drug over a period of several hours at a relatively constant rate.

EXAMPLE 3

This example illustrates another composition of the invention incorporating additional ingredients.

A sustained release composition was prepared by the general procedure disclosed above having the following composition:

| PEG-8000 | 27% |
|---|---|
| Palmitic acid | 13% |
| PEG 400 monostearate | 10% |
| PEO (MW 5 × $10^6$) | 0.1% |
| Cornstarch | 49.8% |
| Clonidine HCl | 0.1% |

The molten mixture was poured onto a surface and allowed to cool and solidify. The solid material was then granulated and fed into an injection molding machine to form dosage forms according to the invention.

EXAMPLE 4

This example illustrates the preparation of dosage forms whose release rate varies with pH.

Uncoated dosage forms of the following composition were prepared by the procedure of Example 1 above:

| PEG-8000 | 2.8 g |
|---|---|
| Myristic acid | 1.1 g |
| Starch | 1.6 g |
| Sodium bicarbonate | 0.5 g |
| Indomethacin | 2.0 g |

Simulated gastric fluid was prepared by dissolving 2 g of sodium chloride and 3.2 g of pepsin in 7 ml of hydrochloric acid, then diluting the solution to a volume of 1000 ml. The pH of the SGF was about 1.2.

The dosage forms were tested by the procedure of Example 1 in SIF and SGF. It was found that the rate of drug release was substantially faster in SIF.

EXAMPLE 5

This example illustrates preparation of PEG esters.

PEG-8000 was melted in a vessel equipped with a stirrer and heated to 100° C. An amount of myristyl chloride equivalent to one half of the terminal hydroxyl groups of the PEG was melted and added dropwise to the molten PEG with continuous stirring. Chloroform was added to the mixture and the solution was filtered through filter paper (Whatman No. 4) and allowed to stand overnight to evaporate the solvent. The remaining solvent was evaporated the next day by heating at 60° C. The material so obtained was a hard waxy solid having a melting point of about 60° C.

EXAMPLE 6

This example illustrates the preparation of dosage forms of the invention using various drugs.

Sustained release compositions were prepared by the general procedure disclosed above having the following compositions:

| A | PEG (MW 3,350) | 35% |
|---|---|---|
|   | Stearyl alcohol | 15% |
|   | Theophylline | 50% |
| B | PEG 8000 | 30% |
|   | Myristic acid | 20% |
|   | PEG 400 monostearate | 10% |
|   | PEO (MW 5 × 10$^6$) | 0.1% |
|   | Corn starch | 24.9% |
|   | Dipyridamole | 15% |
| C | PEG-8000 | 2.8 g |
|   | Myristic acid | 1.2 g |
|   | Starch | 1.8 g |
|   | Hydrochlorothiazide | 50 mg |
| D | PEG-8000 | 1.5 g |
|   | Myristic acid | 0.6 g |
|   | Starch | 0.9 g |
|   | Furosemide | 1.0 g |
| E | PEG-8000 | 5% |
|   | Myristic acid | 10% |
|   | Starch | 15% |
|   | Flubiprofen | 70% |
| F | PEG-1000 | 0.7 g |
|   | PEG-8000 | 0.7 g |
|   | PEG-20000 | 0.7 g |
|   | Myristic acid | 1.0 g |
|   | Palmitic acid | 1.0 g |
|   | Stearic acid | 1.0 g |
|   | Starch | 0.9 g |
|   | KCl | 6.0 g |
| G | PEG-8000 | 50% |
|   | Glyceryl monostearate | 5% |
|   | Starch | 20% |
|   | Dipyridamole | 25% |

EXAMPLE 7

This example illustrates a dosage form of this invention incorporating a pesticide.

A composition of the invention was prepared by the procedure of Example 1 having the following composition:

| PEG-8000 | 37.5% |
|---|---|
| Myristic acid | 15.0% |
| Starch | 22.5% |
| Carbofuran | 25.0% |

Cylindrical dosage forms (uncoated) were prepared by the procedure of Example 1. These dosage forms were found to erode over a period of about one day in an aqueous environment.

EXAMPLE 8

This example illustrates the preparation of a coated dosage form of the invention.

A composition was prepared by the procedure of Example 1 having the following composition:

| PEG-3350 | 27% |
|---|---|
| Myristic acid | 13% |
| PEG-400 distearate | 2% |
| Potato starch | 13% |
| Quinidine.2H$_2$SO$_4$ | 45% |

After mixing the molten composition was poured onto a surface and allowed to cool and harden. The hardened composition was then granulated and introduced into an extrusion apparatus. A cylindrical stream was extruded from the apparatus and coextruded therewith, so as to form a continuous coating over the extruded cylinder, was a liquid impervious coating having the following composition:

| Cetyl alcohol | 99% |
|---|---|
| Diethyl phthalate | 1% |

The extruded cylinder was then cut into dosage forms having a length of about 10 mm and dosage forms were tested as in Example 1 and found to release the drug over a period of time.

EXAMPLE 9

This example illustrates controlled release compositions of this invention having a relatively rapid release rate for the bioactive compound contained therein.

Sustained release compositions were prepared by the general procedure disclosed above having the following compositions:

| A | PEG 3350 | 45% |
|---|---|---|
|   | Stearic acid | 5% |
|   | Starch | 25% |
|   | Pseudoephedrine hydrochloride | 25% |
| B | PEG 3350 | 49% |
|   | Stearic acid | 1% |
|   | Starch | 25% |
|   | Pseudoephedrine hydrochloride | 25% |
| C | PEG 3350 | 50% |
|   | Starch | 25% |
|   | Pseudoephedrine hydrochloride | 25% |
| D | PEG 3350 | 45% |
|   | Palmitic acid | 5% |
|   | Starch | 25% |
|   | Pseudoephedrine hydrochloride | 25% |
| E | PEG 3350 | 49.5% |
|   | Palmitic acid | 0.5% |
|   | Starch | 25% |
|   | Pseudoephedrine hydrochloride | 25% |
| F | PEG 3350 | 45% |
|   | Stearyl alcohol | 5% |
|   | Starch | 25% |
|   | Pseudoephedrine hydrochloride | 25% |
| G | PEG 3350 | 48% |
|   | Stearyl alcohol | 2% |
|   | Starch | 25% |
|   | Pseudoephedrine hydrochloride | 25% |
| H | PEG 3350 | 48% |
|   | Stearyl alcohol | 2% |
|   | Starch | 25% |
|   | Pseudoephedrine hydrochloride | 25% |
| I | PEG 3350 | 50% |
|   | Starch | 25% |

| | | |
|---|---|---|
| | -continued | |
| | Theophylline | 25% |

Figure 1:
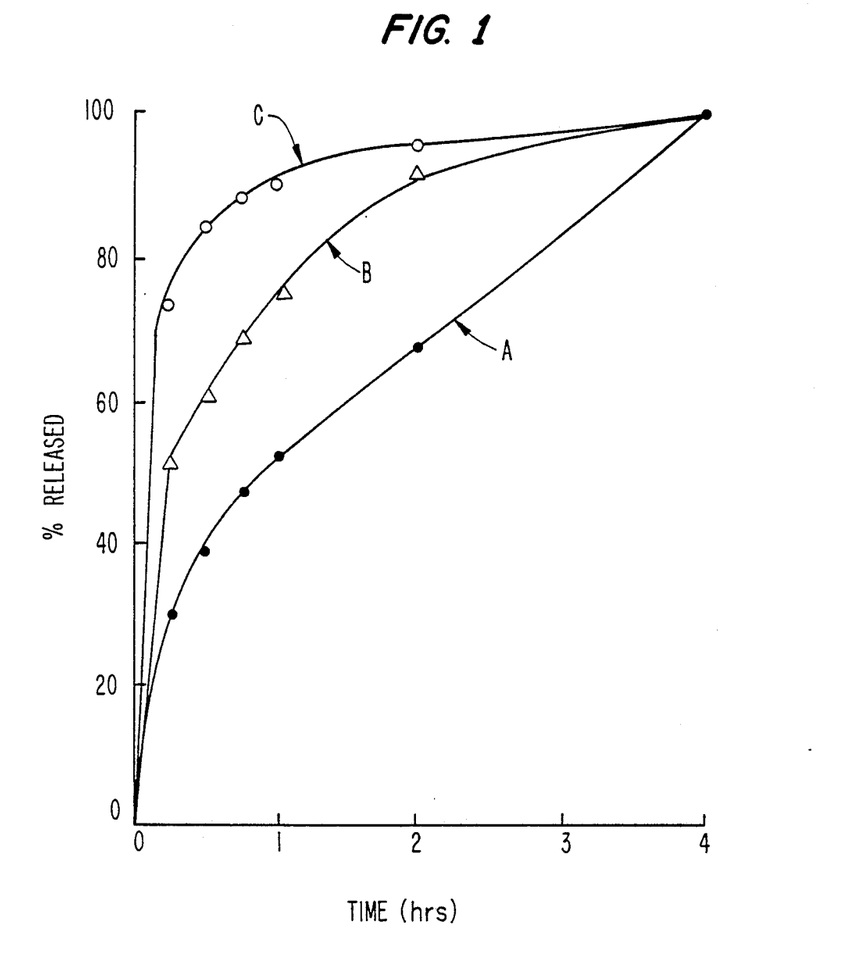
FIG. 1 is a plot of the rate of release of drug from certain of the dosage forms of the invention prepared in Example 9.

The dosage forms were tested by the procedure of Example 1 and were found to release the drug over a period of one-half hour to about four hours. The results for preparations A–C are shown in FIG. 1, where the drug release rates curves are identified by the letter corresponding to the formula in this example. In every case, lower concentrations of amphiphile gave a more rapid release of drug in comparison to similar formulations having a higher concentration of the same amphiphile.

EXAMPLE 10

This example illustrates a number of embodiments of preferred sustained release compositions of this invention incorporating the preferred release rate modifier combination of stearyl alcohol and stearic acid.

Sustained release compositions having the following compositions were prepared by the general procedure described above and uncoated dosage forms were prepared by the procedure of Example 1 and tested by the procedure of that example to determine the kinetics of drug release from the dosage forms into simulated intestinal fluid.

| | | |
|---|---|---|
| A | PEG 3350 | 30% |
| | Stearyl alcohol | 10% |
| | Stearic acid | 5% |
| | PEG(400)monostearate | 5% |
| | Corn starch | 45% |
| | Chlorpheniramine maleate | 5% |
| B | PEG 3350 | 30% |
| | Stearyl alcohol | 10% |
| | Stearic acid | 10% |
| | PEG(400)monostearate | 5% |
| | Corn starch | 39% |
| | Caffeine | 6% |
| C | PEG 3350 | 30.0% |
| | Stearyl alcohol | 10.0% |
| | Stearic acid | 5.0% |
| | PEG(400)monostearate | 5.0% |
| | Corn starch | 35.5% |
| | Colloidal silica | 2.0% |
| | Metoclopramide HCl | 12.5% |
| D | PEG 3350 | 30.0% |
| | Stearyl alcohol | 10.0% |
| | Stearic acid | 10.0% |
| | Corn starch | 42.9% |
| | Colloidal silica | 2.0% |
| | Clonidine HCl | 0.1% |

Figure 2:
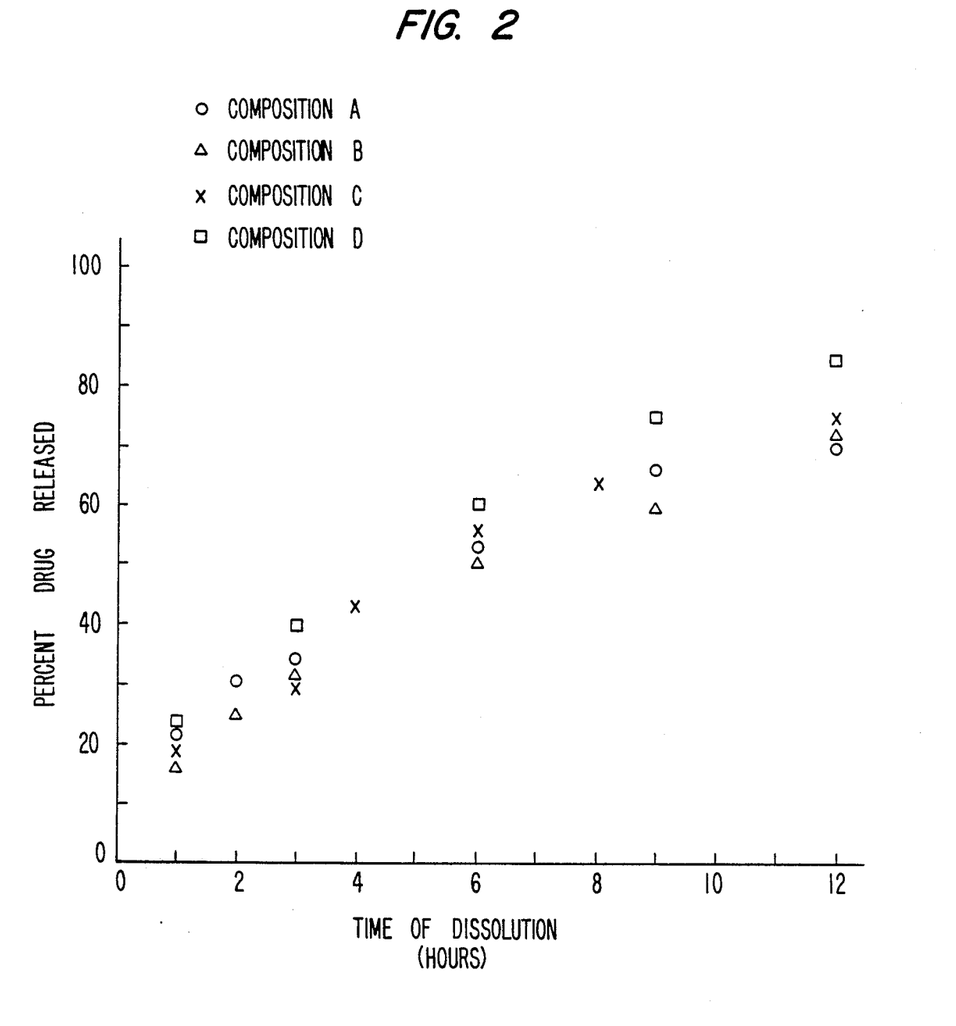
FIG. 2 is a plot of the rate of release of drug from the dosage forms of the invention prepared in Example 10.

For each dosage form, the rate of release of the drug into an aqueous environment was determined. The results are shown in FIG. 2 where the letters correspond to the compositions of this example.

EXAMPLE 11

This example illustrates the effect of pH of the aqueous environment on the release of the drug from dosage forms incorporating the preferred release rate modifier combination of stearyl alcohol and stearic acid.

Sustained release compositions having the following compositions were prepared by the general procedure described above and uncoated dosage forms were prepared by the procedure of Example 1 and tested by the procedure of that example using an aqueous environment of varied pH.

| | | |
|---|---|---|
| A | PEG 3350 | 25% |
| | Stearyl alcohol | 10% |
| | Stearic acid | 5% |
| | PEG(400)monostearate | 5% |
| | Corn starch | 15% |
| | Pseudoephedrine HCl | 40.5% |
| A | PEG 3350 | 25% |
| | Stearyl alcohol | 10% |
| | Stearic acid | 10% |
| | PEG(400)monostearate | 5% |
| | Cimetidine | 50% |

For each dosage form the rate of release of the drug into an aqueous envirnment of pH 7.2 (SIF) and pH 1.2 (SGF) was determined. The results are plotted in FIG. 3, where the letters correspond to the compositions of this example.

Figure 3:
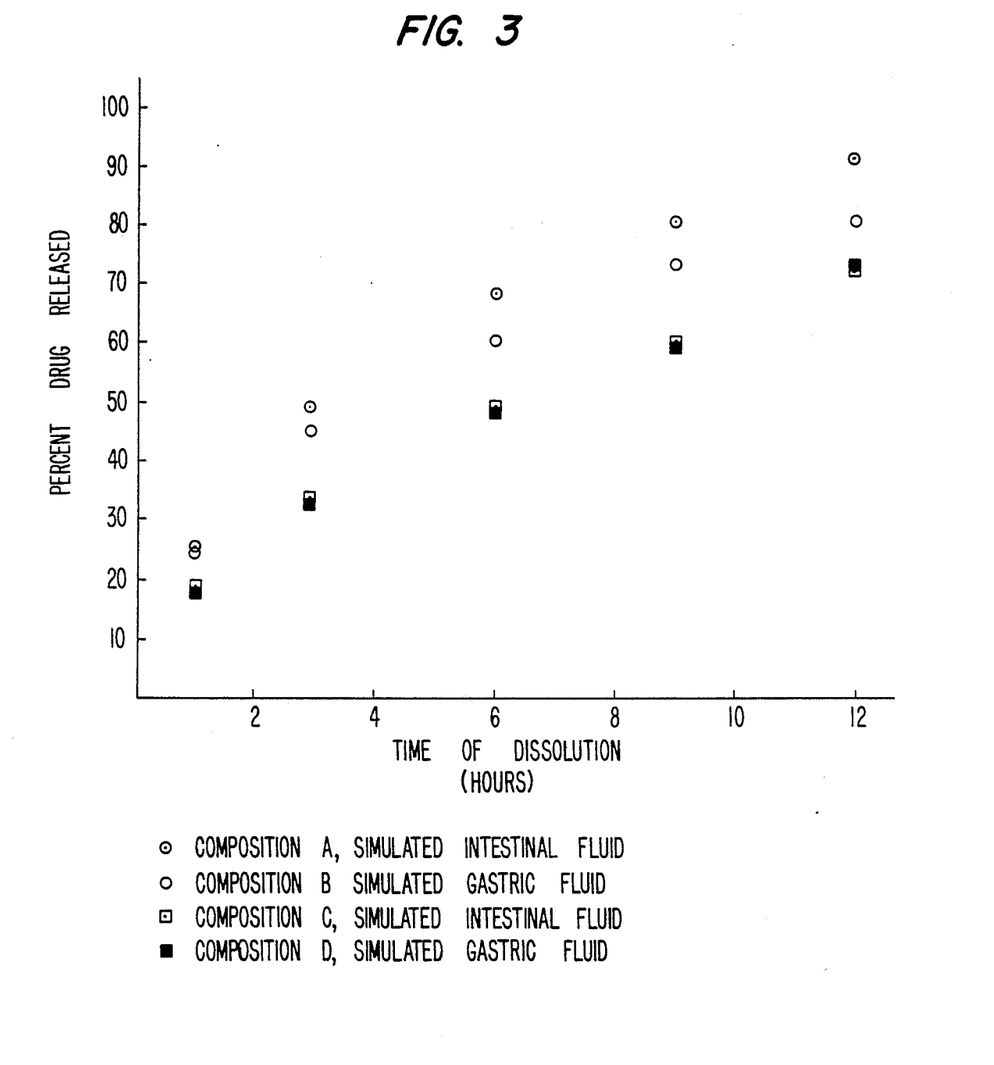
FIG. 3 is a plot of the rate of release of drug from the dosage forms of the invention prepared in Example 11.

These results show that for these preferred embodiments the drug release rate is relatively unaffected by the pH of the aqueous environment.

EXAMPLE 12

This example illustrates the effect of PEG (400) monostearate as an erosion rate modifier when used in conjunction with the preferred release rate modifier combination of stearyl alcohol and stearic acid.

Sustained release compositions having the following compositions were prepared by the general procedure described above and uncoated dosage forms were prepared by the procedure of Example 1 and tested by the procedure of that example to determine the kinetics of drug release from the dosage forms into simulated intestinal fluid.

| | | |
|---|---|---|
| A | PEG 3350 | 30% |
| | Stearyl alcohol | 10% |
| | Stearic acid | 5% |
| | Corn starch | 15% |
| | Pseudoephedrine HCl | 40% |
| B | PEG 3350 | 25% |
| | Stearyl alcohol | 10% |
| | Stearic acid | 5% |
| | PEG (400) monostearate | 5 |
| | Corn starch | 15% |
| | Pseudoephedrine HCl | 40% |

Figure 4:
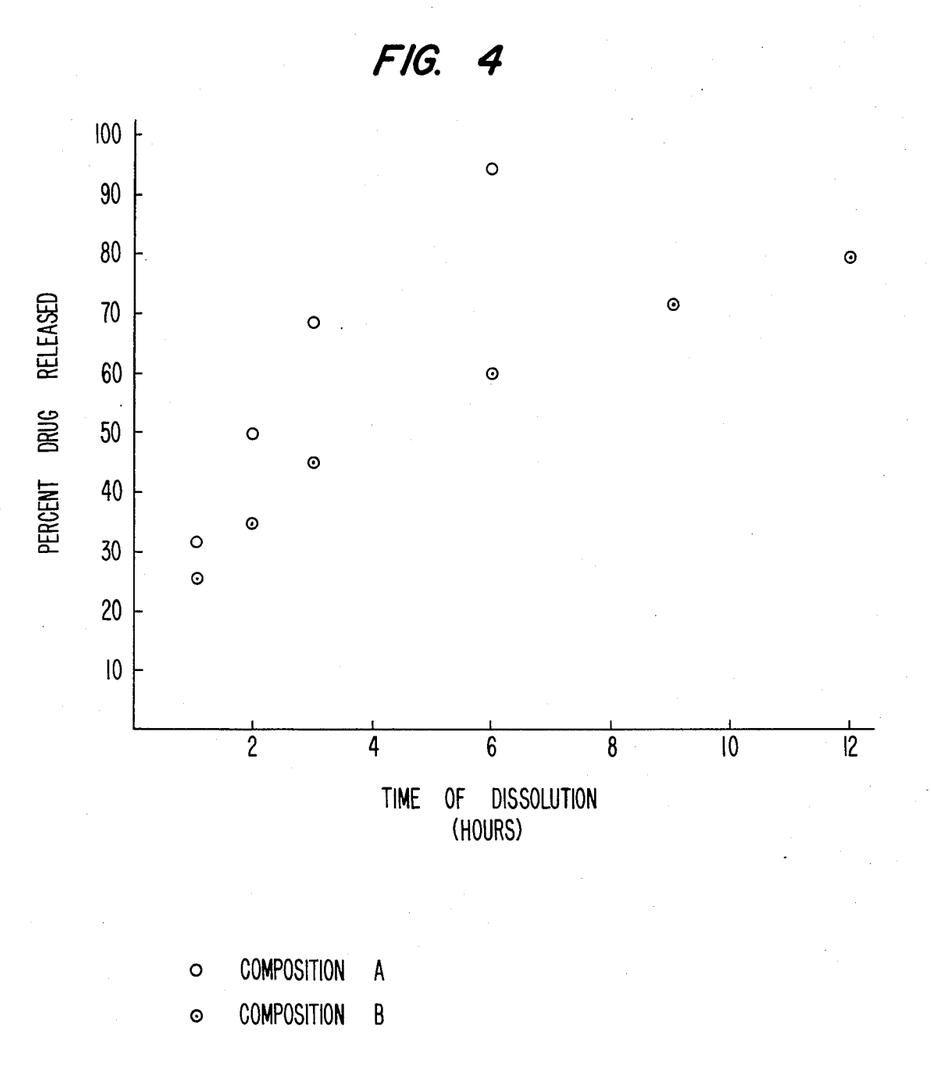
FIG. 4 is a plot of the rate of release of drug from the dosage forms of the invention prepared in Example 12.

For each dosage form, the rate of release of the drug into SIF was determined. The results are shown in FIG. 4, where the letters correspond to the compositions of this example.

EXAMPLE 13

This example illustrates additional embodiments of preferred sustained release compositions of this invention incorporating the preferred release rate modifier combination of stearyl alcohol and stearic acid.

Sustained release compositions having the following compositions were prepared by the general procedure described above and uncoated dosage forms were prepared by the procedure of Example 1 and tested by the procedure of that example.

| | | |
|---|---|---|
| A | PEG 3350 | 30.0% |
| | Stearyl alcohol | 10.0% |
| | Stearic acid | 5.0% |
| | PEG(400)monostearate | 5.0% |
| | Corn starch | 42.5% |
| | Phenylephrine HCl | 5.0% |
| B | PEG 3350 | 28.5% |

| | | |
|---|---|---|
| | Stearyl alcohol | 9.5% |
| | Stearic acid | 4.8% |
| | PEG(400)monostearate | 4.8% |
| | Corn starch | 23.8% |
| | Diphenhydramine | 23.8% |
| C | PEG 3350 | 30.0% |
| | Stearyl alcohol | 10.0% |
| | Stearic acid | 5.0% |
| | PEG(400)monostearate | 5.0% |
| | Corn starch | 15.0% |
| | Phenylpropanolamine HCl | 35.0% |
| D | PEG 3350 | 33.3% |
| | Stearyl alcohol | 11.1% |
| | Stearic acid | 5.6% |
| | PEG(400)monostearate | 5.6% |
| | Disopyramide phosphate | 44.1% |
| E | PEG 3350 | 40.0% |
| | Stearyl alcohol | 10.0% |
| | Stearic acid | 5.0% |
| | PEG(400)monostearate | 5.0% |
| | Penicillin V, Na | 40.0% |
| F | PEG 3350 | 40.0% |
| | Stearyl alcohol | 10.0% |
| | Stearic acid | 5.0% |
| | PEG(400)monostearate | 5.0% |
| | Oxacillin | 40.0% |
| G | PEG 3350 | 40.0% |
| | Stearyl alcohol | 10.0% |
| | Stearic acid | 5.0% |
| | PEG(400)monostearate | 5.0% |
| | Cloxacillin | 40.0% |
| H | PEG 3350 | 40.0% |
| | Stearyl alcohol | 10.0% |
| | Stearic acid | 5.0% |
| | PEG(400)monostearate | 5.0% |
| | Dicloxacillin | 40.0% |
| I | PEG 3350 | 40.0% |
| | Stearyl alcohol | 10.0% |
| | Stearic acid | 5.0% |
| | PEG(400)monostearate | 5.0% |
| | Cefadroxil | 40.0% |
| J | PEG 3350 | 40.0% |
| | Stearyl alcohol | 10.0% |
| | Stearic acid | 5.0% |
| | PEG(400)monostearate | 5.0% |
| | Penicillin G | 40.0% |
| K | PEG 3350 | 33.0% |
| | Stearyl alcohol | 10.0% |
| | Stearic acid | 10.0% |
| | PEG(400)monostearate | 5.0% |
| | Colloidal silica (Syloid 244 FP) | 5.0% |
| | Dipyridamole | 37.0% |
| L | PEG 3350 | 25.0% |
| | Stearyl alcohol | 10.0% |
| | Stearic acid | 10.0% |
| | PEG(400)monostearate | 5.0% |
| | Corn starch | 28.0% |
| | Colloidal silica (Syloid 244 FP) | 2.0% |
| | Propranolol | 20.0% |
| M | PEG 3350 | 25.0% |
| | Stearyl alcohol | 10.0% |
| | Stearic acid | 5.0% |
| | PEG(400)monostearate | 5.0% |
| | Corn starch | 35.0% |
| | Colloidal silica (Syloid 244 FP) | 5.0% |
| | Dextromethorphan HBr | 15.0% |

For all dosage forms given in this example and in Examples 10 and 11, the rate of release of the drug into the aqueous environment was suitable for a 12 hour release of the total dose with 50% release time averaging 6.0 hours with a standard deviation of 2.2 hours.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

What is claimed is:

1. A composition erodible by an aqueous liquid comprising
   5 to 99.5% by weight of a polyethylene glycol having a molecular weight of from about 1000 to about 20,000, and
   95 to 0.5% by weight of an erosion rate modifier component comprising a combination of stearyl alcohol and stearic acid.

2. The composition of claim 1 wherein said stearyl alcohol is present in an amount of about 4% to about 15% by weight and said stearic acid is present in an amount of about 4% to about 13% by weight.

3. The composition of claim 1 wherein said polyethylene glycol has a molecular weight of about 8000.

4. The composition of claim 1 wherein said polyethylene glycol has a molecular weight of about 3350.

5. The composition of claim 1 additionally comprising a substance which increases the compatibility of the polyethylene glycol and the erosion rate modifier.

6. The composition of claim 5 wherein said substance is a polyethylene glycol having a molecular weight from about 200 to about 10000 and having at least one of its terminal OH groups esterified with a $C_{12}$–$C_{20}$ fatty acid.

7. The composition of claim 6 wherein said polyethylene glycol is polyethylene glycol 400.

8. The composition of claim 7 wherein said substance is polyethylene glycol 400 having at least one of its terminal OH groups esterified with stearic acid.

9. The composition of claim 1 additionally comprising a disintegrant.

10. The composition of claim 9 wherein said disintegrant is starch.

11. The composition of claim 1 additionally comprising a molding adjuvant.

12. The composition of claim 11 wherein said molding adjuvant is polyethylene oxide having a molecular weight of 100,000 to 5,000,000.

13. A sustained release composition for releasing a biologically active compound into its surrounding environment comprising said biologically active compound dispersed in a matrix which, when contacted with an aqueous liquid, erodes progressively, said matrix comprising a mixture of
   5 to 99.5% by weight of a polyethylene glycol having a molecular weight of from about 1000 to about 20,000, and
   95 to 0.5% by weight of an erosion rate modifier component comprising a combination of stearyl alcohol and stearic acid.

14. The composition of claim 13 wherein said stearyl alcohol is present in an amount of about 4% to about 13% by weight and said stearic acid is present in an amount of about 4% to about 15% by weight.

15. The composition of claim 13 wherein said polyethylene glycol has a molecular weight of about 8000.

16. The composition of claim 13 wherein said polyethylene glycol has a molecular weight of about 3350.

17. The composition of claim 13 additionally comprising a substance which increases the compatibility of the polyethylene glycol and the erosion rate modifier.

18. The composition of claim 17 wherein said substance is a polyethylene glycol having a molecular weight from about 200 to about 10000 and having at least one of its terminal OH groups esterified with a $C_{12}$—$C_{20}$ fatty acid.

19. The composition of claim 18 wherein said polyethylene glycol is polyethylene glycol 400.

20. The composition of claim 19 wherein said substance is polyethylene glycol 400 having at least one of its terminal OH groups esterified with stearic acid.

21. The composition of claim 13 additionally comprising a disintegrant.

22. The composition of claim 21 wherein said disintegrant is starch.

23. The composition of claim 13 additionally comprising a molding adjuvant.

24. The composition of claim 23 wherein said molding adjuvant is polyethylene oxide having a molecular weight of 100,000 to 5,000,000.

25. A sustained release composition for releasing a biologically active compound into its surrounding environment comprising a pharmaceutically active compound or non-toxic pharmaceutically acceptable salt of said pharmaceutically active compound dispersed in a matrix which, when contacted with an aqueous liquid, erodes progressively, said matrix comprising a mixture of
   5 to 99.5% by weight of a polyethyene glycol having a molecular weight of from about 1000 to about 20,000, and
   95 to 0.5% by weight of an erosion rate modifier component comprising a combination of stearyl alcohol and stearic acid.

26. The composition of claim 25 wherein said stearyl alcohol is present in an amount of about 4% to about 13% by weight and said stearic acid is present in an amount of about 4% to about 15% by weight.

27. The composition of claim 25 wherein said compound is clonidine.

28. The composition of claim 25 wherein said compound is dipyridamole.

29. The composition of claim 25 wherein said compound is hydrochlorothiazide.

30. The composition of claim 25 wherein said compound is furosemide.

31. The composition of claim 25 wherein said compound is indomethacin.

32. The composition of claim 25 wherein said compound is scopolamine.

33. The composition of claim 25 wherein said compound is a bronchodilator.

34. The composition of claim 33 wherein said bronchodilator is theophylline.

35. The composition of claim 25 wherein said compound is quinidine.

36. The composition of claim 25 wherein said compound is naproxen.

37. The composition of claim 25 wherein said compound is propranolol.

38. The composition of claim 25 wherein said compound is a salicylate.

39. The composition of claim 38 wherein said salicylate is aspirin.

40. The composition of claim 25 wherein said compound is nitroglycerin.

41. The composition of claim 25 wherein said compound is isosorbide dinitrate.

42. A sustained release composition for releasing an ecologically active compound into its surrounding environment comprising said ecologically active compound dispersed in a matrix which, when contacted with an aqueous liquid, erodes progressively, said matrix comprising a mixture of
   5 to 99.5% by weight of a polyethylene glycol having a molecular weight of from about 1000 to about 20,000, and
   95 to 0.5% by weight of an erosion rate modifier component comprising a combination of stearyl alcohol and stearic acid.

43. The composition of claim 42 wherein said stearyl alcohol is present in an amount of about 4% to about 15% by weight and said stearic acid is present in an amount of about 4% to about 13% by weight.

44. The composition of claim 42 wherein said ecologically active compound is a fertilizer.

45. The composition of claim 42 wherein said ecologically active compound is a pesticide.

46. The composition of claim 42 wherein said ecologically active compound is an insecticide.

47. The composition of claim 42 wherein said ecologically active compound is an herbicide.

48. A sustained release dosage form for releasing a biologically active compound into an aqueous liquid environment comprising a non-porous solid erodible matrix having dispersed therein a biologically active compound, said matrix comprising a mixture of
   5 to 99.5% by weight of a polyethylene glycol having a molecular weight of from about 1000 to about 20,000, and
   95 to 0.5% by weight of an erosion rate modifier component comprising a combination of stearyl alcohol and stearic acid.

49. The composition of claim 48 wherein said stearyl alcohol is present in an amount of about 4% to about 13% by weight and said stearic acid is present in an amount of about 4% to about 15% by weight.

50. The dosage form of claim 48 wherein said polyethylene glycol has a molecular weight of about 8000.

51. The dosage form of claim 48 wherein said polyethylene glycol has a molecular weight of about 3350.

52. The dosage form of claim 48 additionally comprising a substance which increases the compatibility of the polyethylene glycol and the erosion rate modifier.

53. The dosage form of claim 52 wherein said substance is a polyethylene glycol having a molecular weight from about 200 to about 10000 and having at least one of its terminal OH groups esterified with a $C_{12}$–$C_{20}$ fatty acid.

54. The dosage form of claim 53 wherein said polyethylene glycol is polyethylene glycol 400.

55. The dosage form of claim 54 wherein said substance is polyethylene glycol 400 having at least one of its terminal OH groups esterified with stearic acid.

56. The dosage form of claim 48 additionally comprising a disintegrant.

57. The dosage form of claim 56 wherein said disintegrant is starch.

58. The dosage form of claim 48 additionally comprising a molding adjuvant.

59. The dosage form of claim 58 wherein said molding adjuvant is polyethylene oxide having a molecular weight of 100,000 to 5,000,000.

60. The dosage form of claim 48 wherein said biologically active compound is a pharmaceutically active compound or non-toxic pharmaceutically acceptable salt of said compound and said dosage form contains an effective amount of said compound or said salt.

61. The dosage form of claim 60 wherein said compound is clonidine.

62. The dosage form of claim 60 wherein said compound is dipyridamole.

63. The dosage form of claim 60 wherein said compound is hydrochlorothiazide.

64. The dosage form of claim 60 wherein said compound is furosemide.

65. The dosage form of claim 60 wherein said compound is indomethacin.

66. The dosage form of claim 60 wherein said compound is scopolamine.

67. The dosage form of claim 60 wherein said compound is a bronchodilator.

68. The dosage form of claim 67 wherein said bronchodilator is theophylline.

69. The dosage form of claim 60 wherein said compound is guinidine.

70. The dosage form of claim 60 wherein said compound is naproxen.

71. The dosage form of claim 60 wherein said compound is propranolol.

72. The dosage form of claim 60 wherein said compound is a salicylate.

73. The composition of claim 72 wherein said salicylate is aspirin.

74. The dosage form of claim 60 wherein said compound is nitroglycerin.

75. The dosage form of claim 60 wherein said compound is isosorbide dinitrate.

76. The dosage form of claim 48 wherein said dosage form has the shape of a cylinder.

77. The dosage form of claim 76 wherein said cylinder has a diameter from about 3 mm to about 8 mm.

78. The dosage form of claim 77 wherein said cylinder has a diameter of about 6 mm.

79. The dosage form of claim 76 wherein said cylinder has a length from about 5 mm to about 20 mm.

80. The dosage form of claim 79 wherein said cylinder has a length of about 10 mm.

81. The dosage form of claim 76 additionally comprising at least a partial coating of a liquid impermeable non-self-supporting coating.

82. The dosage form of claim 81 wherein said coating comprises a solid $C_{12}$–$C_{20}$ fatty acid.

83. The dosage form of claim 81 wherein said coating comprises myristic acid.

84. The dosage form of claim 81 wherein said coating comprises palmitic acid.

85. The dosage form of claim 81 wherein said dosage form has a cylindrical shape and is coated on its peripheral cylindrical surface with a liquid-impervious non-self-supporting coating.

* * * * *